United States Patent [19]
Laufer

[11] Patent Number: 6,152,139
[45] Date of Patent: Nov. 28, 2000

[54] DEVICE AND METHOD FOR PREPARING VEINS

[75] Inventor: Michael D. Laufer, Menlo Park, Calif.

[73] Assignee: HeartenMedical, Inc., Menlo Park, Calif.

[21] Appl. No.: 08/788,548

[22] Filed: Jan. 24, 1997

[51] Int. Cl.[7] .................................................. A61B 19/00
[52] U.S. Cl. ............................................ 128/898; 604/500
[58] Field of Search .................... 623/1, 12; 128/898; 424/443, 445; 600/36; 606/4, 159, 194

[56] References Cited

U.S. PATENT DOCUMENTS

| | | |
|---|---|---|
| Re. 31,035 | 9/1982 | Hancock et al. ........................ 623/1 X |
| 3,868,956 | 3/1975 | Alfidi et al. ............................. 606/194 |
| 4,135,494 | 1/1979 | Stoner et al. ............................. 600/36 |
| 4,791,913 | 12/1988 | Maloney . |
| 4,952,215 | 8/1990 | Ouriel et al. . |
| 4,969,890 | 11/1990 | Sugita et al. ........................... 606/192 |
| 5,037,427 | 8/1991 | Harada et al. .......................... 606/108 |
| 5,049,154 | 9/1991 | Quadri . |
| 5,092,872 | 3/1992 | Segalowitz . |
| 5,133,725 | 7/1992 | Quadri . |
| 5,139,506 | 8/1992 | Bush . |
| 5,171,316 | 12/1992 | Mehigan . |
| 5,226,430 | 7/1993 | Spears et al. ........................... 128/898 |
| 5,234,450 | 8/1993 | Segalowitz . |
| 5,284,478 | 2/1994 | Nobles et al. . |
| 5,352,232 | 10/1994 | Cohen . |
| 5,376,376 | 12/1994 | Li ....................................... 606/154 X |
| 5,437,664 | 8/1995 | Cohen et al. . |
| 5,458,596 | 10/1995 | Lax et al. . |
| 5,512,291 | 4/1996 | Li ........................................ 623/12 X |
| 5,514,151 | 5/1996 | Fogarty et al. . |
| 5,522,824 | 6/1996 | Ashby . |
| 5,527,327 | 6/1996 | Louw et al. . |

*Primary Examiner*—V. Millio
*Assistant Examiner*—Kelly O'Hara
*Attorney, Agent, or Firm*—Burns, Doane, Swecker & Mathis L.L.P.

[57] ABSTRACT

A device and method for treating a vein to improve its structural integrity. Heating the vein causes at least a portion of the cross links of the collagen in the vein to unlink/open and subsequently form new cross links after the collagen fibers have realigned. The procedure produces a vein that is less flaccid and more resilient. The lumen can have a larger diameter and a shaped smoother inner surface.

14 Claims, 2 Drawing Sheets

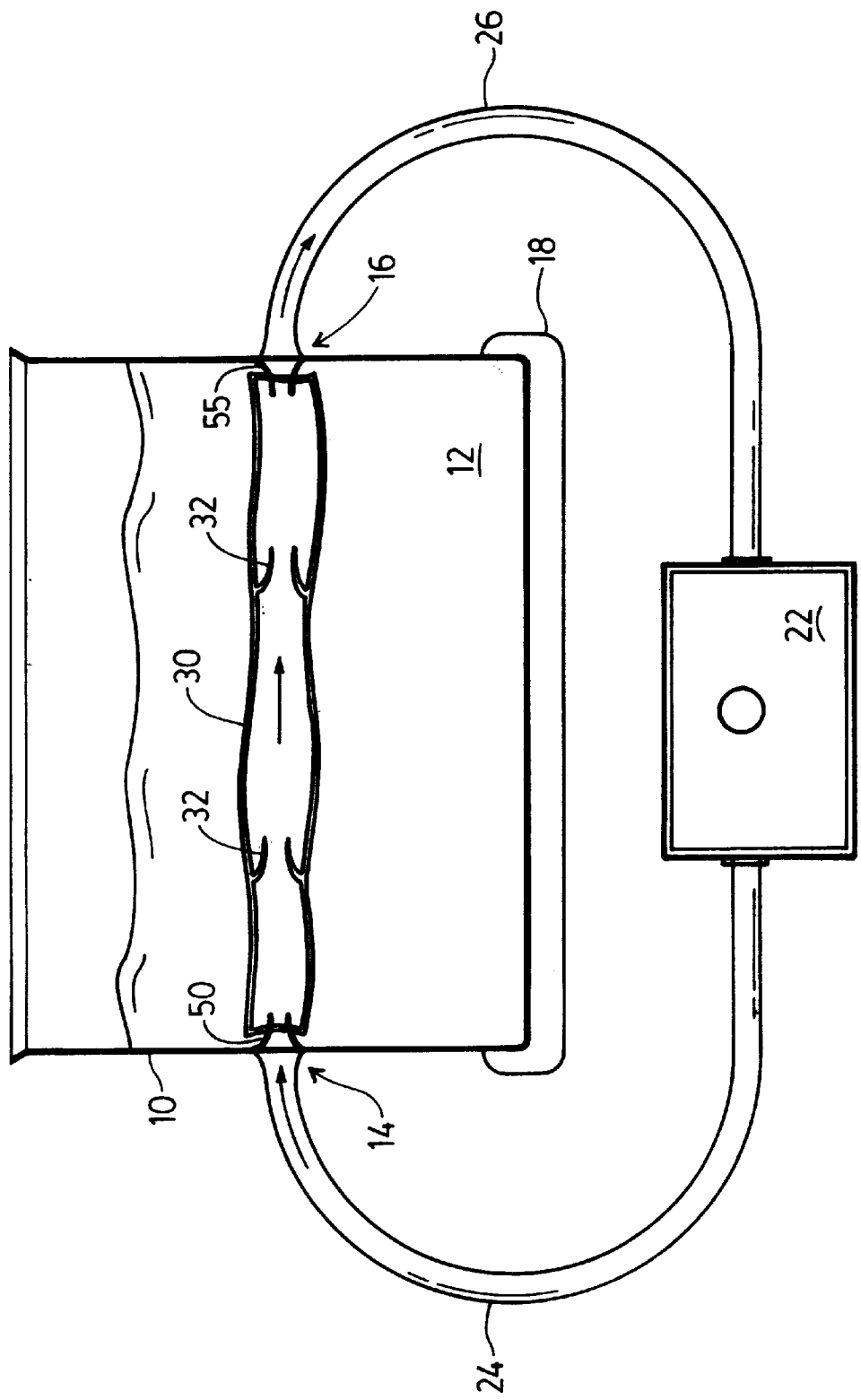
FIG._1.

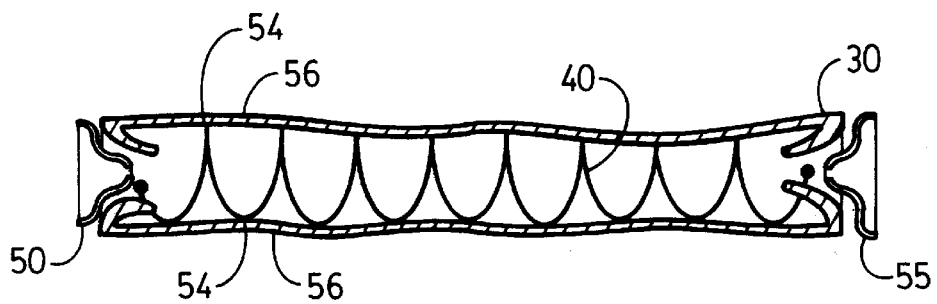
FIG._2.
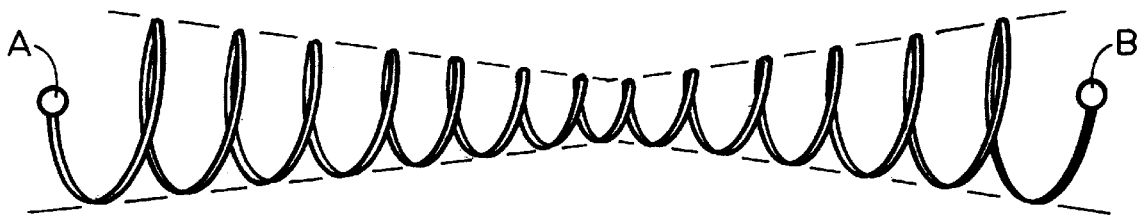
FIG._3.
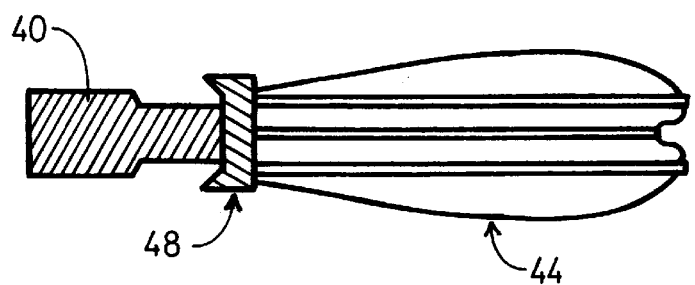
FIG._4.

DEVICE AND METHOD FOR PREPARING VEINS

FIELD OF THE INVENTION

The present invention relates generally to the modification of veins for use in coronary artery bypass graft and other surgical procedures.

BACKGROUND OF THE INVENTION

Many individuals, particularly the elderly, suffer from deposits which clog their arteries, more commonly referred to as atherosclerosis. Quite frequently, these deposits block or restrict the flow of blood in the coronary arteries. This condition may be debilitating or life-threatening to the individual, and corrective measures must be taken. Although some individuals may be treated with medication, in many cases surgery is required. Some arterial deposits may be removed or the arteries dilated with various surgical techniques, but these procedures do not work for every patient for very long. The condition may recur, requiring further action.

One procedure which has proven effective in combating atherosclerosis is to bypass the blocked artery with another blood carrying conduit. Typically material for an arterial bypass is one of the individual's own veins. More particularly, for coronary artery bypass, the saphenous vein is used. There are two ways in which a surgeon may use the individual's own vein. The vein may be harvested from the patient's leg, removed from the patient's body, and turned end for end before resetting the vein back into the body to be used to bypass the blocked artery. Turning the vein end for end ensures that the valves are oriented in the proper direction to allow the flow of blood. The valves in the vein may eventually adhere to the surface of the lumen wall. A second procedure is to employ a valvulotome to lyse or rupture and render incompetent the valves in the bypass vein. Often the use of the valvulotome causes areas of ulcerations in the vein which eventually become atherosclerotic.

When the clogged artery is in the distal arm or leg, an "in situ" bypass is often employed. In this procedure, since the vein is essentially left in place, the valves in the vein must be lysed or ruptured with a valvulotome before being attached to the artery in place of the blocked segment of artery.

Another problem associated with arterial reconstruction using veins is that after the procedure the veins become aneurysmal over time which increases the likelihood that the vein may rupture or become atherosclerotic. The art is in search of methods for improving the structural integrity of veins that are used in surgical procedures.

SUMMARY OF THE INVENTION

The present invention is based in part on the discovery that the structural integrity of veins used in surgical procedures can be improved by subjecting the vein to a sufficient amount of heat to cause at least a portion of the cross links of the collagen in the vein to open and subsequently form new cross links after the collagen fibers have realigned. This procedure, which can be done after the vein has been removed from the patient, modifies the vein so that it becomes less flaccid and more resilient. The vein will also have a smoother inner surface and larger lumen with a more uniform, rounder cross section. The technique can also be implemented with the vein left in place in the case of an "in situ" procedure.

In one aspect, the invention is directed to a method that includes the steps of positioning a vein in an aqueous fluid; causing a pressure differential between the lumen of the vein and the exterior surface of the vein such that the wall of the lumen is at a higher pressure than the exterior surface of the vein; and heating the vein.

Preferably, the heating step comprises raising the temperature of the aqueous fluid to a temperature between about 70° and about 95° C. In a preferred embodiment, the method includes the step of circulating an aqueous fluid through the lumen with sufficient force and flow to cause the valve leaflets of the vein to adhere to the inner wall of the vein during the heating process.

In another aspect, the invention is directed to a device for treating a vein which includes a container that has a reservoir that holds a first aqueous fluid and wherein the vein is placed; means for circulating a second aqueous solution into and out of the lumen of the vein; and means for heating the vein.

In a preferred embodiment, a coil is inserted in the lumen so that the inner surface of the vein will have a spiral contour after the heating procedure. This will cause vortex-like turbulent blood flow along the inner surface of the lumen after the vein has been grafted. It is expected that this will reduce the rate of deposition of fatty substances in the inner wall of the vein and increase distal perfusion.

In a further aspect, the invention is directed to a method of grafting a modified vein into an artery that comprises the steps of:

(a) selecting a segment of vein from an individual;
(b) heating the segment of vein to a temperature sufficient to cause collagen in the segment of vein to undergo a structural transformation by a process comprising:
 (i) inserting a heating device that comprises a heating element inside the lumen of the segment of vein;
 (ii) energizing the heating device and
 (iii) removing the device;
(c) interrupting, entering, or removing a segment of arterial vessel from an artery of the individual; and
(d) grafting the segment of vein to the artery.

In yet another aspect, the invention is directed to an in situ arterialization method of grafting a modified vein into an artery that includes the steps of:

(a) isolating a segment of vein from an appendage of an individual;
(b) heating the segment of vein to a temperature sufficient to cause collagen in the segment of vein to undergo a structural transformation by a process comprising:
 (i) inserting a heating device that comprises a heating element inside the lumen of the segment of vein;
 (ii) energizing the heating device; and
 (iii) removing the heating device;
(c) removing a segment of arterial vessel from an artery located in the said appendage of the individual; and
(d) grafting the segment of vein to the artery.

In a preferred embodiment, the heating device comprises a coil.

In still another aspect, the invention is directed to methods of training a person to graft a vein into the an artery by the above described vein heat treatment technique.

BRIEF DESCRIPTION OF THE DRAWINGS

As used herein, like reference numerals will designate similar elements in the various embodiments of the present invention wherein:

FIG. 1 is a schematic diagram illustrating a device for heating a vein according to the present invention;

FIG. 2 is a schematic illustrating a coil device that is inserted into a vein; and FIGS. 3 and 4 illustrate a coil and heating apparatus for insertion into a vein.

DETAILED DESCRIPTION OF THE PREFERRED EMBODIMENTS

The present invention provides a device and method for effecting change in collagen-containing soft tissue in veins. The invention controls the application of heat within a specific thermal range, and delivers thermal energy to the collagen-containing soft tissue of the vein to cause stabilization of the collagen cross links and contraction of the collagen fibers. New cross links are established. This "arterialization" procedure produces a vein that has greater tensile strength and other physical properties more characteristic of arteries.

FIG. 1 depicts a device that is suitable for implementing the heating process of the present invention. The device includes container 10 that has reservoir 12 for holding an aqueous fluid. As used herein, the term "aqueous fluid" includes water or a water based solution or mixture that is biocompatible with the vein that is undergoing the heating procedure. Blood could be used as the aqueous fluid. A preferred aqueous fluid is a saline solution which reduces the likelihood of osmotic disruption of the cells in the vein.

The container includes ports 14 and 16 through which tubings 24 and 26, respectively, are inserted. The container is in thermal contact with a heating jacket 18. Any suitable heating apparatus such as, for example, a resistive heater can be employed. The invention is contemplated to be implemented with any suitable appliance for applying thermal energy, radiant energy or to otherwise heat the vein tissue. The tubings are part of a circulation system that pumps an aqueous fluid through the vein. The system includes pump 22 which also serves to maintain the aqueous fluid in the vein at a higher pressure vis-a-vis the aqueous fluid in the reservoir. In operation, vein 30 which has been removed from a patient is attached to the ends of the tubings. As is evident, the vein is oriented so that the valves 32 do not block the flow of the aqueous fluid from tubing 24. Optionally, the device can include a support (not shown) to hold the vein in position.

During the heating process, the circulating aqueous fluid is preferably maintained at a temperature between about 20° C. to about 40° C. and more preferably at about 37° C. The aqueous fluid in the reservoir is preferably maintained at a higher temperature typically between about 70° C. and about 95° C., preferably between about 70° C. and about 86° C., and more preferably at about 75° C. The temperature must not be so high as to adversely affect the vein tissue. Specifically, temperatures of about 100° C. will cause denaturation. Depending on the temperature of the heating process, preferably the vein should be exposed to the elevated temperatures for about 20 to 360 seconds and more preferably about 60 to 120 seconds.

The aqueous fluid flowing through the lumen of the vein is preferably maintained at a higher pressure sufficient to cause the lumen to expand slightly. Preferably, the pressure differential is about 10 to about 60 mm Hg, and more preferably about 20–40 mm Hg. It is expected that the lumen will have a more uniform diameter and a smoother surface. If the pressure is sufficiently high and/or the flow rate of the aqueous fluid in the lumen is fast enough, the leaflets of the valves will come into physical contact with the inner wall of the vein. It is expected that during the heating process, the leaflets will become attached to the inner wall. It is understood that while the valves of the vein used in this illustration have not been removed by a valvutome before being attached to the tubings, removing the valves is an optional procedure, if desired.

During the heating process, a structural transfiguration of the collagen fibers in the vein occurs which results in a vein having the before-mentioned improved structural features. Generally, the requisite structural transformation to the vein is substantially complete when the "arterialized" vein does not collapse when flow is reduced in the lumen of the vein and the coil (if employed) is removed. Specifically, the term "non-collapsed vein" refers to a heat treated vein wherein the lumen is substantially unobstructed even when the vein is free standing when placed on a surface and/or in an aqueous fluid. In other words, a non-collapsed vein prepared by the inventive technique has sufficient patency so that the inner walls of the lumen do not come into physical contact with each other. Preferably, the heat treated vein has a substantially uniform lumen diameter and/or cross section. Although the veins to be treated by the invention are not limited in length, heat treated veins having these non-collapsed vein physical properties will preferably be about 2 to 20 cm and more preferably about 5 to 10 cm in length. After the heat treatment, the vein is ready for use in a surgical procedure.

In another embodiment of the invention as shown in FIG. 2, a coil 40 is placed inside the lumen and in physical contact with the inner wall of vein 30. The vein is folded at the proximal and distal ends so as to be readily secured by flanges 50 and 55, respectively of the heating device shown in FIG. 1. During the heating process, it is expected that the surface of inner wall of the lumen will develop an indentation or groove that has a contour substantially matching that of the series of spirals of the coil. It is further expected that the surface of inner wall will retain the indentation after the heating process. The result will be that blood flow through the modified vein will have vortex-like flow characteristics along the inner wall of the lumen. These flow patterns should reduce the deposition rate of fatty substance in the inner wall and improve distal flow.

It is also expected that the physical presence of the coil will cause a slight outward protrusion along the outer surface 54 of the vein adjacent to that part of the inner surface of the lumen that comes into contact with the spirals of the coil. Furthermore, it is expected that the heating process will cause vein tissue that is located between the spirals, e.g., at positions 56, to shrink and cause tissue convexity inward between the spirals. These structural changes to the vein may improve the flow of blood through the vein by contributing to the formation of the above described turbulent flow characteristics.

The coil as depicted in FIG. 2 is preferably an expanding coil. A preferred coil is illustrated in FIG. 3 which includes a wire that has been wound into a series of loops. In this configuration which has ends A and B, by twisting one end of the coil and keeping the other stationary, the length of the coil will shorten while the diameter of the coil will increase. By inserting this coil into a vessel, e.g., segment of vein, and twisting it in this manner, the coil will expand and come into contact with the inner surface of the lumen. Each end of the coil is also covered with a nodule which prevents the ends from inadvertently puncturing the vein. The coil can be constructed from a plurality of wires, e.g., two-strand double-helix configuration. This will create more grooves on the inner wall of the lumen as described above.

In a further embodiment, coil 40 can serve as a heating device with a source of energy that is employed in place of or in conjunction with thermal energy from the aqueous fluid in the reservoir. The coil can comprise a heating element such as, for example, an RF electrode. When the coil is positioned inside the lumen, an RF generator (not shown) is activated to provide suitable RF energy, preferably at a selected frequency in the range of 10 MHz to 1000 MHz. When the coil comprises a unipolar electrode, an outer ground electrode (not shown) is in contact with the aqueous fluid in the reservoir. The emitted energy is converted within the vein tissue into heat causing a rise in the tissue temperature to about 60° C. to about 80° C. RF energy is no longer applied after there has been sufficient transformation of the vein.

Substantial transformation may be achieved very rapidly, depending upon the specific treatment conditions. Because the transformation can proceed at a rather rapid rate, the RF energy is preferably applied at low power levels. The RF power is preferably applied in the range of about 1 watt to about 10 watts. Preferably, the RF energy is applied for a length of time in the range of about 10 seconds to about 120 seconds. The frequency of the RF energy is selected to minimize tissue disruption at the treatment site. Suitable RF power sources are commercially available and well known to those skilled in the art. In one embodiment of the invention RF generator 36 has a single channel, delivering approximately 1 to 10 watts of RF energy and possessing continuous flow capability. The rate of transformation of the vein can be controlled, for instance, by increasing or decreasing the aqueous fluid flow rate through the lumen, and varying the energy delivered to the heating element.

The coil with the heating element can be made to provide protection against overheating of the vein. In one embodiment, the heating element has a shape memory capability such that the heating element self-straightens or collapses if the heating element or the aqueous fluid in the lumen reaches a temperature above 98° C. such that contact with the inner surface would be lost, and the current flow through the heating element would become nearly zero. Other techniques, for example, temperature monitoring, impedance monitoring, and ultrasonic pulse echoing, can be utilized in a system which shuts down the application of energy from the heating element to the vein when sufficient transformation of the vein is detected. Monitoring these values for feedback control of the energy applied also prevents denaturation. The amount of energy applied can be decreased or eliminated (manually or automatically) if the temperature of the vein reaches a preset critical temperature. For example, the temperature of the aqueous fluid, tissue of vein 30, or of coil 40 is monitored and the energy being applied adjusted accordingly. The technician or physician can, if desired, override the feedback control system. A microprocessor can be included and incorporated into the feedback control system to switch the power on and off, as well as modulate the power. The microprocessor can serve as a controller to watch the temperature and modulate the power in order to prevent denaturation.

Although the invention has been described as using RF energy for energizing the heating element, it is to be understood that other forms of energy such as alternating current, microwaves, ultrasound, and light (either coherent or incoherent sources) can be used, and that the thermal energy generated from a resistive coil, a hot fluid element (e.g., liquids, gases, combinations of liquids and gases) a curie point element, or similar elements can be used as well.

The heating device as illustrated in FIG. 2 comprises an expandable and collapsible coil, however, it is understood that the heating element can have other curled configurations (e.g., helix, corkscrew, spiral, twist, etc.). Preferably, the heating element of the device is fabricated from a biocompatible material with at least partial shape memory capability, such as a nickel-titanium-based alloy. The heating element in accordance with any of the embodiments can be a number of different materials including but not limited to conductive polymer, stainless steel, platinum, other noble metals, or shape memory alloy, such as Nitinol™ which is a nickel-titanium-alloy, available from Raychem Corporation, Menlo Park, Calif.

FIG. 4 illustrates another heating device suitable for insertion into the lumen of a vein. The device includes a handle 40 to which is attached a plurality of electrodes configured as flat bands 44. In a preferred embodiment, the two ends of each band are attached to handle 40 so that the bands form a plurality of elongated loop structures emanating from the handle. The electrodes can be energized to heat the vein. In practice, the plurality of electrode flat bands are inserted in the lumen of the vein and the vein is secured with a nut 48, clamp, or other similar device. The heating device is preferably configured so that the outer surfaces of the bands come into contact with the inner surface of the lumen.

The coils that comprise heating elements can be employed in arterialization in situ of the vein by the inventive heating process. This technique is particularly suited for distal arm and leg bypasses that are referred as "in situ bypass." By arterialization "in situ" is meant that the segment of vein to be treated is left in place in the appendage (i.e., arm or leg) where the diseased artery to be removed is located. In arterialization in situ, a segment of vein is first isolated in a patient, then the vein from which the segment is taken is sealed by conventional means. The segment then undergoes the heating process whereby a coil comprising a heating element is inserted into the lumen and energized. Following heat treatment as described previously, the segment of vein can be grafted to an artery in place of a diseased or otherwise non-functional segment of artery.

The heating element of any of the embodiments can be made to provide protection against overheating of the vein tissue. Techniques, including, for example, temperature monitoring or electrical characteristic monitoring (e.g., impedance), can be utilized in a system which shuts down the application of energy to the heating element to avoid ablating the tissue or damaging healthy tissue. The feedback control system can be designed to be overridden, if desired. A microprocessor can be included and incorporated into the feedback control system to switch the power on and off, as well as modulate the power. The microprocessor can serve as a controller to watch the temperature and modulate the power in order to avoid over-heating the tissue. Furthermore, the system can include auditory or visual feedback indicators for signalling when shrinkage, temperature, or other variables are occurring and also when any has reached or exceeded desired conditions.

The invention is also directed to the demonstration or instruction of the inventive surgical techniques including, but not limited to, actual instructions involving patients, audio-visual presentations, animal demonstrations, and the like.

While several particular embodiments of the invention have been illustrated and described, it will be apparent that various modifications can be made without departing from the spirit and scope of the invention. Accordingly, it is not intended that the invention be limited, except as by the appended claims.

What is claimed is:

1. An ex vivo method of treating a vein that comprises the step of:

heating the vein to a temperature sufficient to cause collagen in the vein to undergo a structural transformation.

2. The method of claim 1 wherein the vein is placed in an aqueous fluid that is heated to a temperature in the range between about 70° C. and about 95° C.

3. The method of claim 2 wherein the vein is heated for about 20 seconds to about 360 seconds.

4. The method of claim 1 wherein the step of heating the vein comprises:

positioning a vein in a first aqueous fluid;

causing a pressure differential between an inner surface of the lumen of the vein and an exterior surface of the vein such that the inner surface of the lumen is at a higher pressure than the exterior surface of the vein; and heating the vein.

5. The method of claim 4 wherein the step of heating the vein comprises raising the temperature of the first aqueous fluid to an elevated temperature of about 70° C. to about 95° C.

6. The method of claim 5 further comprising circulating a second aqueous fluid through the lumen of the vein wherein the second aqueous fluid is at a temperature that is lower than that of the first aqueous fluid.

7. The method of claim 5 wherein the vein is heated at the elevated temperature for about 20 seconds to about 360 seconds.

8. The method of claim 4 wherein the inner surface of the lumen of the vein is at a pressure that is higher than that of the exterior surface of the vein to cause a pressure differential of about 10 mm Hg to 60 mm Hg.

9. The method of claim 4 wherein the vein is positioned in a saline solution.

10. The method of claim 4 further comprising positioning a coil inside the lumen of the vein which comes into contact with the inner surface of the lumen.

11. The method of claim 4 wherein the pressure differential causes the interior of the lumen to have a substantially uniform diameter.

12. The method of claim 4 wherein the vein is connected via two ports of a tubing which contains a second aqueous fluid and which is connected to a pump.

13. The method of claim 12 wherein the inner surface of the lumen is at a pressure that is higher than that of the exterior surface of the vein to cause a pressure differential of about 10 mm Hg to 60 mm Hg.

14. The method of claim 1 wherein the heating causes sufficient structural transformation whereby the vein is rendered non-collapsible.

* * * * *